(12) United States Patent
Tanaka et al.

(10) Patent No.: US 7,592,473 B2
(45) Date of Patent: *Sep. 22, 2009

(54) METHOD OF SYNTHESIZING COMPOUND

(75) Inventors: Hirohisa Tanaka, Shiga (JP); Kimiyoshi Kaneko, Tokyo (JP)

(73) Assignees: Daihatsu Motor Co., Ltd., Osaka (JP); Hokko Chemical Industry Co., Ltd., Tokyo (JP)

( * ) Notice: Subject to any disclaimer, the term of this patent is extended or adjusted under 35 U.S.C. 154(b) by 130 days.

This patent is subject to a terminal disclaimer.

(21) Appl. No.: 11/886,531

(22) PCT Filed: Mar. 16, 2006

(86) PCT No.: PCT/JP2006/305206

§ 371 (c)(1),
(2), (4) Date: Sep. 17, 2007

(87) PCT Pub. No.: WO2006/098398

PCT Pub. Date: Sep. 21, 2006

(65) Prior Publication Data

US 2008/0177112 A1    Jul. 24, 2008

(30) Foreign Application Priority Data

Mar. 17, 2005   (JP) .............................. 2005-077801

(51) Int. Cl.
*C07F 17/02*   (2006.01)

(52) U.S. Cl. ..................... 556/136; 556/7; 556/466; 554/220; 562/492

(58) Field of Classification Search ................ 554/220; 562/492; 556/7, 136, 466

See application file for complete search history.

(56) References Cited

U.S. PATENT DOCUMENTS

2002/0128478 A1*   9/2002   Krska et al. .................. 544/59

2004/0192542 A1    9/2004   Choudary et al.
2005/0215804 A1*   9/2005   Ley et al. ..................... 554/220

FOREIGN PATENT DOCUMENTS

| EP | 1 728 766 A1 | 12/2006 |
| JP | 2004-298802 | 10/2004 |
| JP | 2005-314355 | 11/2005 |
| WO | WO 2005/090238 A1 | 9/2005 |

OTHER PUBLICATIONS

Martin D. Smith et al., "Palladium-containing perovskites: recoverable and reuseable catalysts for Suzuki couplings," Chem. Comm., 2003, p. 2652-2653, vol. 11, No. 21, UK.

Martin D. Smith et al., "Heterogeneous or Homogenous? A case study involving Palladium-containing perovskites in the Suzuki Reaction," Adv. Synth. Catl., 2005, vol. 347, UK.

* cited by examiner

*Primary Examiner*—Peter G. O'Sullivan
*Assistant Examiner*—Sudhakar Katakam
(74) *Attorney, Agent, or Firm*—Akerman Senterfitt; Jean C. Edwards, Esq.

(57) ABSTRACT

In order to provide a method of synthesizing a compound in which activity of a catalyst is maintained even when the catalyst is recovered after the completion of the coupling reaction using a palladium-containing perovskite-type composite oxide as the catalyst and used repeatedly and the reaction can be carried out in a high yield, a palladium-containing perovskite-type composite oxide is used as a synthesis reaction catalyst and a reaction solvent containing an alkoxy alcohol is used as a reaction solvent in Suzuki Cross-Couplings given by the following general formula (15).

[Chemical Formula 4]

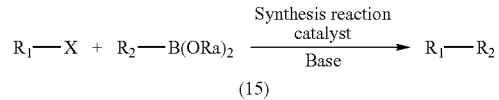

(15)

4 Claims, No Drawings

METHOD OF SYNTHESIZING COMPOUND

The present invention is a 35 USC 371 national stage entry of PCT/JP2006/305206, filed Mar. 16, 2006 which claims priority from Japanese Patent Application No. 2005-077801, filed Mar. 17, 2005, the contents of which are herein incorporated by reference in their entirety.

The present invention relates to a method of synthesizing a compound and, more particularly, to a method of synthesizing a compound through a coupling reaction.

BACKGROUND OF THE INVENTION

There have hitherto been proposed various examples of the reaction of a catalyst containing palladium as active species, and it is reported that a catalyst comprising a palladium-containing perovskite-type composite oxide is highly active as a catalyst for Suzuki Cross-Couplings, and that also the catalyst can be recovered and reused after the completion of the reaction. In Suzuki Cross-Couplings, isopropyl alcohol/water is used as a reaction solvent (see the following Non Patent Document 1). Non Patent Document 1: Martin D. Smith et al., Chemical Communications. pp. 2652-2653, 7 Nov., 2003

SUMMARY OF THE INVENTION

In Suzuki Cross-Couplings, the palladium-containing perovskite-type composite oxide used as a catalyst is expensive, and therefore it is required that the palladium-containing perovskite-type composite oxide is recovered after the completion of the reaction and then reused so as to reduce the production cost. In order to reuse the catalyst, however, it is indispensable that activity of the catalyst is maintained even when used repeatedly for a long period.

An object of the present invention is to provide a method of synthesizing a compound in which activity of a catalyst is maintained even when the catalyst is recovered after the completion of the coupling reaction using a palladium-containing perovskite-type composite oxide as the catalyst and used repeatedly and the reaction can be carried out in a high yield.

Solution to the Problems

To achieve the above object, the method of synthesizing a compound of the present invention comprises reacting a compound represented by the following general formula (1) with a compound represented by the general formula (2) or a compound represented by the general formula (3) in the presence of a palladium-containing perovskite-type composite oxide using a reaction solvent containing an alkoxy alcohol:

$$R_1—X \qquad (1)$$

wherein $R_1$ represents an aryl group which may have a substituent, a heterocyclic group which may have a substituent, or an alkenyl group which may have a substituent; and X represents a halogen atom, a trifluoromethanesulfonyloxy group, a p-toluenesulfonyloxy group or a methanesulfonyloxy group, $$R_2-M \qquad (2)$$

wherein R2 represents an aryl group which may have a substituent, a heterocyclic group which may have a substituent, or an alkenyl group which may have a substituent; M represents a —B(ORa)$_2$— group or a —Sn(Rb)$_3$ group; Ra represents a hydrogen atom or an alkyl group which may have a substituent; and Rb represents an alkyl group, and instead of Ra, a ring including —OBO— may be formed through an arylene group which may have a substituent or an alkylene group which may have a substituent, both of which serve as a bond of —OBO—, and $$R_3HC=CR_4R_5 \qquad (3)$$

wherein $R_3$, $R_4$ and $R_5$ each independently represents a hydrogen atom, an alkyl group which may have a substituent, an aryl group which may have a substituent, and a carboxylic acid derivative, an acid amide derivative or a cyano group.

Also, in the method of synthesizing a compound of the present invention, it is preferred that a compound represented by the above general formula (1) is reacted with a compound represented by the above general formula (2) in the presence of a palladium-containing perovskite-type composite oxide, and that $R_1$ is an aryl group which may have a substituent and X is a halogen atom in the general formula (1), and $R_2$ is an aryl group which may have a substituent and M is a —B(ORa)$_2$ group in the general formula (2).

In the method of synthesizing a compound of the present invention, the alkoxy alcohol is preferably at least one selected from the group consisting of 2-methoxy-1-propanol, 2-ethoxy-1-propanol, ethylene glycol monomethyl ether, ethylene glycol monoethyl ether and ethylene glycol isopropyl ether.

In the method of synthesizing a compound of the present invention, the palladium-containing perofskite-type composite oxide is preferably represented by the following general formula (4):

$$A_xB_{(1-y)}Pd_yO_{3+\sigma} \qquad (4)$$

wherein A represents at least one element selected from rare earth elements and alkaline earth metals; B represents at least one element selected from transition elements (excluding rare earth elements and Pd) and Al; x represents an atomic ratio satisfying the following relation: $1.0 \leq x \leq 1.3$; y represents an atomic ratio satisfying the following relation: $0 < y \leq 0.5$; and σ represents an oxygen excess amount.

In the method of synthesizing a compound of the present invention, by using a reaction solvent containing an alkoxy alcohol in the coupling reaction in the presence of a palladium-containing perovskite-type composite oxide, activity of a catalyst can be maintained even when the catalyst is recovered after the completion of the reaction and used repeatedly and the reaction can be carried out in a high yield.

DESCRIPTION OF THE INVENTION

The method of synthesizing a compound of the present invention is carried out in the presence of a palladium (Pd)-containing perovskite-type composite oxide.

In the present invention, the palladium-containing perovskite-type composite oxide is typically a composite oxide having a perovskite-type structure represented by the general formula ABO$_3$ and can be used without any limitation as long as the perovskite-type composite oxide contains palladium.

The perovskite-type composite oxide containing palladium includes, for example, a perovskite-type composite oxide containing palladium as a composition so that palladium constitutes a constituent element of the perovskite-type composite oxide and, for example, a palladium-supporting perovskite-type composite oxide, in which palladium is supported on a perovskite-type composite oxide later.

The perovskite-type composite oxide containing palladium as a composition is, for example, represented by the following general formula (4):

$$A_xB_{(1-y)}Pd_yO_{3+\sigma} \quad (4)$$

wherein A represents at least one element selected from rare earth elements and alkaline earth metals; B represents at least one element selected from transition elements (excluding rare earth elements and Pd) and Al; x represents an atomic ratio satisfying the following relation: $1.0 \leqq x \leqq 1.3$; y represents an atomic ratio satisfying the following relation: $0 < y \leqq 0.5$; and σ represents an oxygen excess amount.

In the general formula (4), examples of the rare earth elements represented by A include Sc (scandium), Y (yttrium), La (lanthanum), Ce (cerium), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium) and Lu (lutetium), of which Y, La, Ce, Pr and Nd are preferred, and La is more preferred.

These rare earth elements can be used alone or in combination.

Also in the general formula (4), examples of the alkaline earth metals represented by A include Be (beryllium), Mg (magnesium), Ca (calcium), Sr (strontium), Ba (barium) and Ra (radium).

These alkaline earth metals can be used alone or in combination.

In the palladium-containing perovskite-type composite oxide of the present invention, A is preferably selected from rare earth elements. Also, an atomic ratio x of A satisfies the following relation: $1.0 \leqq x \leqq 1.3$. When x is less than 1.0, it may be difficult to dissolve Pd to form a solid solution at a high rate stably. When x exceeds 1.3, by-products other than the perovskite-type composite oxide may be produced.

In the general formula (4), examples of transition elements excluding rare earth elements and Pd, which are represented by B, include elements having atomic numbers 22 (Ti) through 30 (Zn), atomic numbers of 40 (Zr) through 48 (Cd), and atomic numbers of 72 (Hf) through 80 (Hg) in the Periodic Table of Elements (IUPAC, 1990), excluding Pd.

Examples of the transition elements (excluding rare earth elements and Pd) and Al, which are represented by B, are preferably Cr (chromium), Mn (manganese), Fe (iron), Co (cobalt), Ni (nickel), Cu (copper), Zn (zinc) and Al (aluminum), of which Fe and Co are more preferred.

The atomic ratio y of Pd satisfies the following relation: $0 < y \leqq 0.5$, that is, y is 0.5 or less. When the atomic ratio of Pd exceeds 0.5, it may be difficult to dissolve Pd to form a solid solution and also the cost is inevitably increased.

Therefore, B, elements other than Pd (elements selected from transition elements (excluding rare earth elements and Pd) and Al) is contained in an atomic ratio satisfying 1-y, that is to say, an atomic ratio satisfying the remainder of Pd (1-y).

Incidentally, σ represents an oxygen excess amount, and more specifically, it represents an excessive atomic ratio of oxygen that is generated as a result of excessive constituent elements on the site A as compared with A:B:O=1:1:3, which is a theoretical constituent ratio of the perovskite-type composite oxide.

These perovskite-type composite oxides containing palladium as the composition can be prepared according to any appropriate method for preparing a composite oxide without any limitation. Examples thereof include a coprecipitation method, a citrate complex method and an alkoxide method.

In the coprecipitation method, for example, an aqueous mixed salt solution is prepared, which contains salts of the above-mentioned respective elements in the stoichiometric ratio, a neutralizing agent is added to the aqueous mixed salt solution and/or the aqueous mixed salt solution is added to the neutralizing agent for coprecipitation thereof, and the resulting coprecipitate is dried and subjected to a heat treatment.

Examples of the salts of the respective elements include inorganic salts such as sulfates, nitrates, chlorides, and phosphates; and organic salts such as acetates and oxalates. The aqueous mixed salt solution can be prepared, for example, by adding the salts of the respective elements to water so as to establish a predetermined stoichiometric ratio and mixing them with stirring.

Then, the aqueous mixed salt solution is coprecipitated by adding the neutralizing agent thereto. Alternatively, a coprecipitate can be obtained by adding dropwise the aqueous mixed salt solution to an aqueous solution containing an excessive amount of neutralizing agent. The neutralizing agent includes, for example, ammonia; organic base including amines such as triethylamine and pyridine; and inorganic bases such as caustic soda, caustic potash, potassium carbonate and ammonium carbonate. The neutralizing agent is added in an amount such that the pH of the solution after the addition of the neutralizing agent is adjusted within a range about from 6 to 14, and preferably about from 8 to 12.

The resulting coprecipitate is washed with water, if necessary, dried by vacuum drying or forced-air drying, and subjected to a primary heat treatment at about 400 to 1,000° C., preferably at about 600 to 950° C., and furthermore subjected to a secondary heat treatment at about 900 to 1,100° C., if necessary. Thus, a perovskite-type composite oxide can be prepared.

In the citrate complex method, for example, an aqueous solution of a citrate salt mixture is prepared by mixing citric acid and salts of the respective elements in an amount establishing the predetermined stoichiometric ratio. The aqueous solution of the citrate salt mixture is thoroughly dried to form a citrate complex of the respective elements. The resulting citrate complex is provisionally baked and then subjected to a heat treatment.

Example of the salts of the respective elements include the salts of the same kinds as those mentioned above. The aqueous solution of the citrate salt mixture is, for example, prepared by preparing an aqueous mixed salt solution in the same manner as above and adding an aqueous solution of citric acid to the aqueous mixed salt solution.

Then, the aqueous solution of the citrate salt mixture is thoroughly dried to form a citrate complex of the above-mentioned respective elements. The drying process is carried out at a temperature at which the formed citrate complex is not decomposed, for example, from room temperature to about 150° C. to remove water swiftly. Consequently, the above citrate complex of the respective elements can be formed.

The resulting citrate complex is then provisionally baked and heat treated. The provisional baking may be, for example, carried out at a temperature of 250° C. or higher in vacuum or in an inert atmosphere. Then, the provisionally baked substance is subjected to a primary heat treatment at about 300 to 1,000° C., and preferably at about 600 to 950° C., and furthermore if necessary, followed by a secondary heat treatment at about 900 to 1,100° C. to obtain a perovskite-type composite oxide.

In the alkoxide method, for example, an alkoxide mixed solution is prepared, which contains alkoxides of the respective elements excluding Pd and other noble metals in the stoichiometric ratio. The alkoxide mixed solution is precipitated on hydrolysis by adding an aqueous solution containing salts of noble metals including Pd thereto. The resulting precipitate is dried and then subjected to a heat treatment.

Examples of the alkoxides of the respective elements include alcoholates each comprising the respective elements and an alkoxy such as methoxy, ethoxy, propoxy, isopropoxy or butoxy; and alkoxy alcoholates of the respective elements represented by the following general formula (5):

$$E[OCH(R_6)\text{—}(CH_2)_i\text{—}OR_7]_j \qquad (5)$$

wherein E represents the respective elements; $R_6$ represents a hydrogen atom or an alkyl group having 1 to 4 carbon atoms; $R_7$ represents an alkyl group having 1 to 4 carbon atoms; i represents an integer of 1 to 3; and j represents an integer of 2 to 3.

More specific examples of the alkoxy alcoholates include methoxyethylate, methoxypropylate, methoxybutylate, ethoxyethylate, ethoxypropylate, propoxyethylate and butoxyethylate.

The alkoxide mixed solution is prepared, for example, by adding an alkoxide of the respective elements to an organic solvent in an amount that establishes the above stoichiometric ratio and mixing them with stirring.

The organic solvent is not specifically limited, as long as it can dissolve an alkoxide of the respective elements. Examples of such organic solvents include aromatic hydrocarbons, aliphatic hydrocarbons, alcohols, ketones and esters. Aromatic hydrocarbons such as benzene, toluene and xylene are preferred.

Then, the alkoxide mixed solution is precipitated by adding an aqueous solution containing salts of the noble metals including Pd in the predetermined stoichiometric ratio. Examples of the aqueous solution containing salts of the noble metals including Pd include an aqueous solution of nitrate, aqueous solution of chloride, aqueous solution of hexaammine chloride, aqueous solution of dinitrodiammine nitrate, aqueous solution of hexachloro acid hydrate and potassium cyanide salt.

The resulting precipitate is dried, for example, by vacuum drying or forced-air drying and is subjected to a primary heat treatment at about 400 to 1,000° C., preferably at about 500 to 850° C., and furthermore if necessary, followed by a secondary heat treatment at about 900 to 1,100° C. Thus, a perovskite-type composite oxide is prepared.

In such an alkoxide method, the composite oxide may be alternatively prepared in the following manner. A solution containing organometallic salts of the noble metals including Pd is added to the above-mentioned alkoxide mixed solution to prepare a homogenous mixed solution. The homogenous mixed solution is precipitated by adding water thereto. The resulting precipitate is dried and then subjected to a heat treatment.

Examples of the organometallic salts of the noble metals including Pd include: carboxylate of the noble metals including Pd, which is derived from acetate, propionate or the like; and metal chelate complexes of the noble metals including Pd such as diketone complexes of the noble metals including Pd, which is derived from diketone compounds represented by the following general formula (6) or (7):

$$R_8COCHR_{10}COR_9 \qquad (6)$$

wherein $R_8$ represents an alkyl group having 1 to 4 carbon atoms, a fluoroalkyl group having 1 to 4 carbon atoms or an aryl group; $R_9$ represents an alkyl group having 1 to 4 carbon atoms, a fluoroalkyl group having 1 to 4 carbon atoms, an aryl group or an alkyloxy group having 1 to 4 carbon atoms; and $R_{10}$ represents a hydrogen atom or an alkyl group having 1 to 4 carbon atoms; and $$CH_3CH(COR_{11})_2 \qquad (7)$$

wherein $R_{11}$ represents a hydrogen atom or an alkyl group having 1 to 4 carbon atoms.

In the above general formulas (6) and (7), examples of the alkyl group having 1 to 4 carbon atoms represented by $R_8$, $R_9$, $R_{10}$ and $R_{11}$ include methyl, ethyl, propyl, isopropyl, n-butyl, s-butyl and t-butyl. Examples of the fluoroalkyl group having 1 to 4 carbon atoms represented by $R_8$ and $R_9$ include trifluoromethyl. Examples of the aryl group represented by $R_8$ and $R_9$ include phenyl. Examples of the alkyloxy group having 1 to 4 carbon atoms represented by $R_9$ include methoxy, ethoxy, propoxy, isopropoxy, n-butoxy, s-butoxy and t-butoxy.

Specific examples of the diketone compound include 2,4-pentanedione, 2,4-hexanedione, 2,2-dimethyl-3,5-hexanedione, 1-phenyl-1,3-butanedione, 1-trifluoromethyl-1,3-butanedione, hexafluoroacetylacetone, 1,3-diphenyl-1,3-propanedione, dipivaloylmethane, methyl acetoacetate, ethyl acetoacetate and t-butyl acetoacetate.

The solution containing the organometallic salts of the noble metals including Pd can be prepared, for example, by adding an organometallic salt of the noble metals including Pd to an organic solvent in an amount that establishes the above-mentioned stoichiometric ratio, and mixing them with stirring. The organic solvent can be any of the above organic solvents.

The prepared solution containing organometallic salts of the noble metals including Pd is mixed with the above alkoxide mixed solution, and the resulting homogenous mixed solution is precipitated by adding water thereto. The resulting precipitate is dried by vacuum drying or forced-air drying, for example, and is subjected to a primary heat treatment at about 400 to 1,000° C., and preferably at about 500 to 850° C., and furthermore if necessary, followed by a secondary heat treatment at about 900 to 1,100° C. Thus, a perovskite-type composite oxide is prepared.

Also, the perovskite-type composite oxide supporting palladium includes, for example, those in which Pd is supported on a perovskite-type composite oxide of the general formula (8):

$$ABO_3 \qquad (8)$$

wherein A represents at least one element selected from rare earth elements and alkaline earth metals; and B represents at least one element selected from transition elements (excluding rare earth elements and Pd) and Al.

In the general formula (8), rare earth elements and alkaline earth metals represented by A and transition elements (excluding rare earth elements and Pd) and Al represented by B include the same as those described above.

Also, such a perovskite-type composite oxide can be produced by an appropriate method for preparing a composite oxide according to the above method, for example, a coprecipitation method, a citrate complex method and an alkoxide method. In case of using an alkoxide method, a mixed alkoxide solution may be hydrolyzed by adding water.

In order to support palladium on the resulting perovskite-type composite oxide, a known method can be used without any limitation. For example, a solution of a salt containing palladium is prepared and the perovskite-type composite oxide may be impregnated with this salt-containing solution and then baked. The amount of palladium to be supported on the perovskite-type composite oxide is, for example, 20 parts by weight or less, and preferably from 0.5 to 5 parts by weight, based on 100 parts by weight of the perovskite-type composite oxide.

As the palladium-containing perovskite-type composite oxide used in the method of synthesizing a compound of the present invention, a perovskite-type composite oxide containing palladium as a composition is preferably used among the above-described perovskite-type composite oxides.

Also, palladium may be further supported on the palladium-containing perovskite-type composite oxide. Palladium can be further supported on the perovskite-type composite oxide containing palladium as a composition in the same manner as in case of supporting palladium on the above perovskite-type composite oxide. The amount of palladium to be supported on the perovskite-type composite oxide containing palladium as a composition is, for example, 10 parts by weight or less, and preferably from 0.1 to 5 parts by weight, based on 100 parts by weight of the perovskite-type composite oxide containing palladium as a composition.

In the perovskite-type composite oxide containing palladium as a composition, those represented by the following general formula (9), particularly those represented by the following general formula (10), are preferably used:

wherein A represents at least one element selected from rare earth elements; A' represents at least one element selected from alkaline earth metals; B represents at least one element selected from transition elements (excluding rare earth elements and Pd) and Al; y represents an atomic ratio satisfying the following relation: $0<y\leq0.5$; w represents an atomic ratio satisfying the following relation: $0\leq w\leq0.5$; v represents an atomic ratio satisfying the following relation: $1.0\leq v+w\leq1.3$; and σ represents an oxygen excess amount, and

wherein A represents at least one element selected from Y, La, Ce, Pr and Nd; B represents at least one element selected from Mn, Fe, Co and Al; x represents an atomic ratio satisfying the following relation: $1.0<x\leq1.3$; y represents an atomic ratio satisfying the following relation: $0<y\leq0.5$; and σ represents an oxygen excess amount.

More specific examples of the perovskite-type composite oxide containing palladium as a composition include $La_{1.00}Fe_{0.57}Co_{0.38}Pd_{0.05}O_3$, $La_{0.9}Ce_{0.1}Fe_{0.57}Co_{0.38}Pd_{0.05}O_3$, $La_{1.00}Fe_{0.95}Pd_{0.05}O_3$, $La_{1.00}Co_{0.95}Pd_{0.05}O_3$, $La_{0.9}Ce_{0.1}Al_{0.95}Pd_{0.05}O_3$, $La_{1.00}Fe_{0.57}Mn_{0.38}Pd_{0.05}O_3$, $La_{1.00}Mn_{0.95}Pd_{0.05}O_3$, $La_{1.05}Fe_{0.57}Co_{0.38}Pd_{0.05}O_{3+\sigma}$ and $La_{1.02}Fe_{0.95}Pd_{0.05}O_{3+\sigma}$.

In the method of synthesizing a compound of the present invention, a compound represented by the following general formula (1) is reacted with a compound represented by the following general formula (2) or a compound represented by the following general formula (3) in the presence of the above the perovskite-type composite oxide containing palladium reaction catalyst using alkoxy alcohol:

$$R_1-X \quad (1)$$

wherein $R_1$ represents an aryl group which may have a substituent, a heterocyclic group which may have a substituent, or an alkenyl group which may have a substituent; and X represents a halogen atom, a trifluoromethanesulfonyloxy group, a p-toluenesulfonyloxy group or a methanesulfonyloxy group, $$R_2-M \quad (3)$$

wherein $R_2$ represents an aryl group which may have a substituent, a heterocyclic group which may have a substituent, or an alkenyl group which may have a substituent; M represents a —$B(ORa)_2$ group or a —$Sn(Rb)_3$ group; Ra represents a hydrogen atom or an alkyl group which may have a substituent; and Rb represents an alkyl group, and instead of Ra, a ring including —OBO— may be formed through an arylene group which may have a substituent or an alkylene group which may have a substituent, both of which serve as a bond of —OBO—, and $$R_3HC=CR_4R_5 \quad (3)$$

wherein $R_3$, $R_4$ and $R_5$ each independently represents a hydrogen atom, an alkyl group which may have a substituent, an aryl group which may have a substituent, a carboxylic acid derivative, an acid amide derivative or a cyano group.

Examples of an aryl group of the aryl group which may have a substituent, which is represented by $R_1$ in the general formula (1), $R_2$ in the general formula (2) and $R_3$, $R_4$ and $R_5$ in the general formula (3), include aryl groups having 6 to 14 carbon atoms such as phenyl, tolyl, xylyl, biphenyl, naphthyl, anthryl, phenanthryl and azulenyl.

The substituent of the aryl group is not specifically limited, and examples of the substituent include such as hydrocarbon groups and hetero atom-containing hydrocarbon groups according to the purposes and applications. Examples thereof include alkyl groups having 1 to 4 carbon atoms such as methyl, ethyl, propyl, isopropyl, butyl, isobutyl, sec-butyl and tert-butyl; allenyl groups having 2 to 4 carbon atoms such as vinyl, 1-methylvinyl, 1-propenyl and allyl; alkynyl groups having 2 to 4 carbon atoms such as ethynyl, 1-propynyl and 1-propargyl; cycloalkyl groups having 3 to 6 carbon atoms such as cyclopropyl, cyclobutyl, cyclopentyl and cyclohexyl; cycloalkenyl groups having 5 to 7 carbon atoms such as cyclopentenyl and cyclohexenyl; aralkyl groups having 7 to 11 carbon atoms such as benzyl, α-methylbenzyl and phenetyl; phenyl group; alkoxy groups having 1 to 6 carbon atoms such as methoxy, ethoxy, propoxy, iso-propoxy, n-butoxy, iso-butoxy, sec-butoxy and tert-butoxy; phenoxy group; alkanoyl groups having 1 to 6 carbon atoms such as formyl, acetyl, propionyl, n-butyryl and iso-butyryl; benzoyl group; alkanoyloxy groups having 1 to 6 carbon atoms such as formyloxy, acetyloxy, propionyloxy, n-butyryloxy and iso-butyryloxy; benzoyloxy group; carboxyl group; alkoxycarbonyl groups having 2 to 7 carbon atoms such as methoxycarbonyl, ethoxycarbonyl, n-propoxycarbonyl, iso-propoxycarbonyl, n-butoxycarbonyl, isobutoxycarbonyl and tert-butoxycarbonyl; carbamoyl groups; N-mono-$C_{1-4}$ alkyl-carbamoyl groups such as N-methylcarbamoyl, N-ethylcarbamoyl, N-propylcarbamoyl, N-isopropylcarbamoyl and N-butylcarbamoyl; N,N-di-$C_{1-4}$ alkylcarbamoyl groups such as N,N-dimethylcarbamoyl, N,N-diethylcarbamoyl, N,N-dipropylcarbamoyl and N,N-dibutylcarbamoyl; cyclic aminocarbonyl groups such as 1-aziridinylcarbonyl, 1-azetidinylcarbonyl, 1-pyrolidinylcarbonyl, 1-piperidinylcarbonyl, N-methylpiperadinylcarbonyl and morpholinocarbonyl; halogen atoms such as fluorine, chlorine, bromine and iodine; mono-, di- or tri-halogeno-$C_{1-4}$ alkyl groups such as chloromethyl, dichloromethyl, trifluoromethyl and trifluoroethyl; oxo group; amidino group; imino group; amino group; mono-$C_{1-4}$ alkylamino groups such as methylamino, ethylamino, propylamino, isopropylamino and butylamino; di-$C_{1-4}$ alkylamino groups such as dimethylamino, diethylamino, dipropylamino, diisopropylamino and dibutylamino; 3 to 6-membered cyclic amino groups containing carbon atoms, a nitrogen atom and optionally 1 to 3 hetero atoms selected from oxygen atom, sulfur atom, nitrogen atom and the like, such as aziridinyl, azetidinyl, pyrolidinyl, pyrolinyl, pyrolyl, imidazolyl, pyrazolyl, imidazolydinyl, piperidino, morpholino, dihydropyridyl, pyridyl, N-methylpiperadinyl and N-ethylpiperadinyl; alkanoyl amido groups having 1 to 6 carbon atoms such as formamide, acetamide, trifluoroacetamide, propionylamide, butyrylamide and isobutyrylamide; benzamide group; carbamoylamino group; N—$C_{1-4}$ alkylcarbamoylamino groups such as N-methylcarbamoylamino, N-ethylcarbamoylamino, N-propylcarbamoylamino, N-isopropylcarbamoylamino and N-butylcarbamoylamino; N,N-di-$C_{1-4}$ alkylcarbamoylamino groups such as N,N-dimethylcarbamoylamino, N,N-diethylcarbamoylamino, N,N-dipropylcarbamoylamino and N,N-dibutylcarbamoylamino; alkylenedioxy groups having 1 to 3 carbon atoms such as methylenedioxy and ethylenedioxy; hydroxyl group; epoxy group (—O—); nitro group; cyano group; mercapto group; sulfo group; sulfino group; phosphono group; sulfamoyl group; monoalkylsulfamoyl groups having 1 to 6 carbon atoms such as N-methylsulfamoyl, N-ethylsulfamoyl, N-propylsulfamoyl, N-isopropylsulfamoyl, and N-butylsulfamoyl; di-$C_{1-4}$ alkylsulfamoyl groups such as N,N-dimethylsulfamoyl, N,N-diethylsulfamoyl, N,N-dipropylsulfamoyl and N,N-dibutylsulfamoyl; alkylthio groups having 1 to 6 carbon atoms such as methylthio, ethylthio, propylthio, isopropylthio, n-butylthio, sec-butylthio and tert-butylthio; phenylthio group; alkylsulfinyl groups having 1 to 6 carbon atoms such as methylsulfinyl, ethylsulfinyl, propylsulfinyl and butylsulfinyl; phenylsulfinyl group; alkylsulfonyl groups having 1 to 6 carbon atoms such as methylsulfonyl, ethylsulfonyl, propylsulfonyl and butylsulfonyl; and phenylsulfonyl group. The above groups may be substituted with 1 to 5 of these substituents.

Examples of a heterocyclic group of heterocyclic groups which may have a substituent represented by $R_1$ in the general formula (1) and $R_2$ in the general formula (2) include 5-membered cyclic groups containing, other than carbon atoms, 1 to 4 hetero atoms selected from oxygen atom, sulfur atom, nitrogen atom and the like, such as 2- or 3-thienyl, 2- or 3-furyl, 2- or 3-pyronyl, 2-, 3- or 4-pyridyl, 2-, 4- or 5-oxazolyl, 2-, 4- or 5-thiazolyl, 3, 4- or 5-pirazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3, 4-thiadiazolyl, 4- or 5-(1,2,3-thiadiazolyl), 1,2,5-thiadiazolyl, 1,2,3-triazolyl, 1,2,4-triazolyl and 1H- or 2H-tetrazolyl; 6-membered cyclic groups containing, other than carbon atoms, 1 to 4 hetero atoms selected from oxygen atom, sulfur atom, nitrogen atom and the like, such as N-oxide-2-, 3- or 4-pyridyl, 2-, 4- or 5-pyrimidinyl, N-oxide-2-, 4- or 5-pyrimidinyl, thiomorpholinyl, morpholinyl, oxoimidazinyl, dioxotriazinyl, pyrolidinyl, piperidinyl, pyranyl, thiopyranyl, 1,4-oxazinyl, 1,4-thiazinyl, 1,3-thiazinyl, piperadinyl, triazinyl, oxotriazinyl, 3- or 4-pyridazinyl, pyrazinyl and N-oxide-3- or 4-pyridazinyl; 5 to 8-membered rings or the condensed rings containing 1 to 4 hetero atoms such as oxygen atom, sulfur atom, nitrogen atom and the like, in addition to carbon atoms in a 2 or 3 cyclic condensed ring group which contains, other than carbon atoms, 1 to 4 hetero atoms selected from oxygen atom, sulfur atom, nitrogen atom and the like, such as benzofuryl, benzothiazolyl, benzoxazolyl, tetrazolo[1,5-b]pyridazinyl, triazolo[4,5-b]pyridazinyl, benzoimidazolyl, quinolyl, isoquinolyl, cinnolinyl, phthalazinyl, quinazolinyl, quinoxalinyl, indolizinyl, quinolizinyl, 1,8-naphthylidinyl, prinyl, pteridinyl, dibenzofuranyl, carbazolyl, acridinyl, phenanthridinyl, chromanyl, benzoxazinyl, phenazinyl, phenothiazinyl and phenoxazinyl.

Substituents of the heterocyclic groups are not specifically limited, and examples include those corresponding to the purposes and applications, such as hydrocarbon group and hetero atom-containing hydrocarbon groups. For example, substituents of the same kinds as those mentioned above are appropriately included. The above groups may be substituted with 1 to 5 of these substituents.

Examples of an alkenyl group of alkenyl groups which may have a substituent represented by $R_1$ in the general formula (1) and $R_2$ in the general formula (2) include alkenyl groups having 2 to 18 carbon atoms such as vinyl, allyl, methalyl, isopropenyl, 1-propenyl, 2-propenyl, 2-methyl-1-propenyl, butenyl, pentenyl, hexenyl, heptynyl, octenyl, nonenyl, decenyl, undecenyl, dodecenyl, tetradecenyl, hexadecenyl and octadecenyl.

Substituents of the alkenyl groups are not specifically limited, and examples include those corresponding to the purposes and applications, such as hydrocarbon group and hetero atom-containing hydrocarbon groups. For example, substituents of the same kinds as those mentioned above are included. The substituents may be substituted with 1 to 5 heterocyclic groups.

Examples of an alkyl group of an alkyl group which may have a substituent represented by Ra in the general formula (2), an alkyl group represented by Rb and an alkyl group of an alkyl group which may have a substituent represented by $R_3$, $R_4$ and $R_5$ in the general formula (3) include alkyl groups having 1 to 18 carbon atoms such as methyl, ethyl, propyl, iso-propyl, n-butyl, iso-butyl, sec-butyl, tert-butyl, pentyl, iso-pentyl, sec-pentyl, hexyl, heptyl, n-octyl, isooctyl, 2-ethylhexyl, nonyl, decyl, isodecyl, dodecyl, tetradecyl, hexadecyl and octadecyl.

Substituents of the alkyl groups are not specifically limited, and examples include those corresponding to the purposes and applications, such as hydrocarbon group and hetero atom-containing hydrocarbon groups. For example, substituents of the same kinds as those mentioned above are included. The substituents may be substituted with 1 to 5 heterocyclic groups.

Examples of an arylene group which may have a substituent, which substitutes for Ra and serves as a bond of —OBO— to form a ring containing —OBO— in the general formula (2), include arylene groups having 6 to 10 carbon atoms such as phenylene, tolylene, xylylene and naphthylene.

Substituents of the arylene groups are not specifically limited, and examples include those corresponding to the purposes and applications, such as hydrocarbon group and hetero atom-containing hydrocarbon groups. For example, substituents of the same kinds as those mentioned above are included. The substituents may be substituted with 1 to 5 heterocyclic groups.

Examples of an alkylene group of an alkylene group which may have a substituent, which serves as a bond of —OBO—, instead of Ra, to form a ring containing —OBO— in the general formula (2), include alkylene groups having 1 to 18 carbon atoms such as methylene, ethylene, propylene, isopropylene, n-butylene, iso-butylene, sec-butylene, tert-butylene, pentylene, iso-pentylene, sec-pentylene, hexylene, heptylene, octylene, 2-ethylhexylene, nonylene, decylene, isodecylene, dodecylene, tetradecylene, hexadecylene and octadecylene.

Substituents of the alkylene groups are not specifically limited, and those corresponding to the purposes and applications, such as hydrocarbon group and hetero atom-containing hydrocarbon groups, are appropriately included. For example, substituents of the same kinds as those mentioned above are included. The substituents may be substituted with 1 to 5 heterocyclic groups.

When, instead of Ra, a ring including —OBO— is formed through the above-mentioned arylene group or alkylene group serving as a bond of —OBO—, the above general formula (2) turns into the following general formula (11):

[Chemical Formula 1]

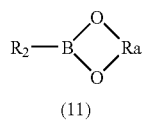

(11)

wherein $R_2$ represents an aryl group which may have a substituent, a heterocyclic group which may have a substituent or an alkenyl group which may have a substituent; and Ra represents an arylene group which may have a substituent or an alkylene group which may have a substituent.

More specifically, the general formula turns into the following general formula (12) when the arylene group which may have a substituent is phenylene, and it turns into the general formula (13) when the alkylene group which may have a substituent is 1,1,2,2-tetramethylethylene.

[Chemical Formula 2]

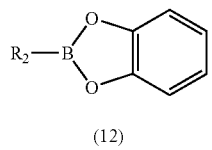

(12)

[Chemical Formula 3]

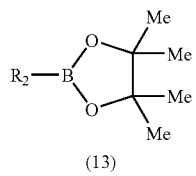

(13)

Examples of a halogen atom represented by X in the general formula (1) include chlorine, bromine and iodine.

Examples of carboxylic acid derivatives represented by $R_3$, $R_4$ and $R_5$ in the general formula (3) include alkoxycarbonyl groups such as methoxycarbonyl (—COOMe), ethoxycarbonyl (—COOEt) and t-butoxycarbonyl (—COOtBu).

In the general formula (3), more specific examples of compounds of such carboxylic acid derivatives are shown in Table 1.

TABLE 1

| $R_3$ | $R_4$ | $R_5$ | Name of compound | Structural formula |
|---|---|---|---|---|
| H | H | $CO_2tBu$ | Tert-butyl acrylate | $H_2C=CHCOOtBu$ |
| H | H | $CO_2Me$ | Methyl acrylate | $H_2C=CHCOOMe$ |
| H | H | $CO_2Et$ | Ethyl acrylate | $H_2C=CHCOOEt$ |
| Me | H | $CO_2Et$ | Ethyl crotonate | $MeCH=CHCOOEt$ |
| Me | Me | $CO_2Et$ | Ethyl tiglate | $MeCH=C(Me)COOEt$ |
| H | Me | $CO_2Et$ | Ethyl methacrylate | $H_2C=C(Me)COOEt$ |

Examples of acid amide derivatives represented by $R_3$, $R_4$ and $R_5$ in the general formula (3) include a carbamoyl (—$CONH_2$) group and N-mono or N,N-dialkylcarbamoyl groups such as N-methylcarbamoyl (—CONHMe) group and N,N-dimethylcarbamoyl (—$CON(Me)_2$) group.

In the general formula (3), more specific examples of compounds of such acid amide derivatives are shown in Table 2.

TABLE 2

| $R_3$ | $R_4$ | $R_5$ | Name of compound | Structural formula |
|---|---|---|---|---|
| H | H | $CONH_2$ | Acrylic acid amide | $H_2C=CHCONH_2$ |
| H | H | CONHMe | N-methylacrylic acid amide | $H_2C=CHCONHMe$ |
| H | H | $CONMe_2$ | N,N-dimethylacrylic acid amide | $H_2C=CHCONMe_2$ |
| Me | H | CONHMe | N-methylcrotonic acid amide | $MeCH=CHCONHMe$ |
| Me | Me | CONHMe | N-methyltiglic acid amide | $MeCH=C(Me)CONHMe$ |
| H | Me | CONHMe | N-methylmethacrylic acid amide | $H_2C=C(Me)CONHMe$ |

In the general formula (3), more specific compounds wherein $R_3$, $R_4$ and $R_5$ are cyano groups are shown in Table 3.

TABLE 3

| $R_3$ | $R_4$ | $R_5$ | Name of compound | Structural formula |
|---|---|---|---|---|
| H | H | CN | Acrylonitrile | $H_2C=CHCN$ |
| Me | H | CN | Crotononitrile | $MeCH=CHCN$ |
| H | Me | CN | Methacrylonitrile | $H_2C=C(Me)CN$ |

In the reaction of a compound represented by the above general formula (1) with a compound represented by the above general formula (2), there is prepared a compound represented by the following general formula (14):

$$R_1—R_2 \quad (14)$$

wherein $R_1$ and $R_2$ represent an aryl group which may have a substituent, a heterocyclic group which may have a substituent or an alkenyl group which may have a substituent.

In the general formula (14), an aryl group which may have a substituent, a heterocyclic group which may have a substituent or an alkenyl group which may have a substituent represented by $R_1$ and $R_2$ are as defined above.

In the reaction of a compound represented by the above general formula (1) with a compound represented by the above general formula (2), when M in the general formula (2) is a —$B(ORa)_2$ group, the method of a synthesizing a compound of the present invention is given by the following reaction scheme (15) called as Suzuki Cross-Couplings.

[Chemical Formula 4]

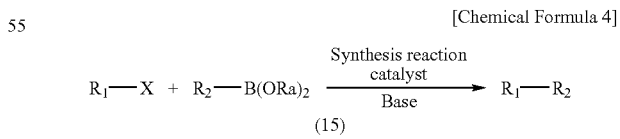

(15)

In the reaction of a compound represented by the above general formula (1) with a compound represented by the above general formula (2), when M in the general formula (2) is a —$Sn(Rb)_3$ group, the method of a synthesizing a compound by the present invention is given by the following reaction scheme (16) called as Stille Cross-Couplings.

[Chemical Formula 5]

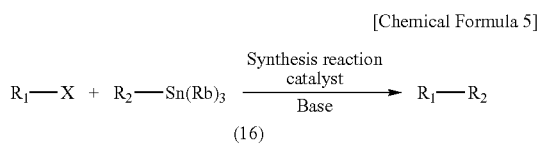

In the reaction of a compound represented by the above general formula (1) with a compound represented by the above general formula (3), there is prepared a compound represented by the following general formula (17):

$$R_1R_3C=CR_5R_4 \quad (17)$$

wherein $R_1$ represents an aryl group which may have a substituent, a heterocyclic group which may have a substituent or an alkenyl group which may have a substituent; $R_3$, $R_4$ and $R_5$ each independently represents a hydrogen atom, an alkyl group which may have a substituent, an aryl group which may have a substituent, a carboxylic acid derivative, an acid amide derivative or a cyano group.

In the general formula (17), an aryl group which may have a substituent, a heterocyclic group which may have a substituent or an alkenyl group which may have a substituent represented by $R_1$, and a hydrogen atom, an alkyl group which may have a substituent, an aryl group which may have a substituent, a carboxylic acid derivative, an acid amide derivative or a cyano group represented by $R_3$, $R_4$ and $R_5$ are as defined above.

In the method of a synthesizing a compound of the present invention, the reaction of a compound represented by the above general formula (1) with a compound represented by the above general formula (3) is given by the following reaction scheme (18) called as Heck Cross-Couplings.

[Chemical Formula 6]

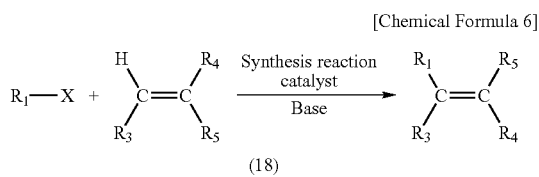

In the method of a synthesizing a compound of the present invention, in the above reaction schemes (15), (16) and (18), a compound represented by the above general formula (1) and a compound represented by the above general formula (2) or (3) are reacted in the presence of the above mentioned palladium-containing perovskite-type composite oxide and a base using a reaction solvent containing an alkoxy alcohol.

In this reaction, examples of the base include inorganic salts such as hydroxides such as sodium hydroxide and potassium hydroxide; carbonates such as sodium carbonate ($Na_2CO_3$), potassium carbonate ($K_2CO_3$) and cesium carbonate ($Cs_2CO_3$); acetates such as sodium acetate and potassium acetate; phosphates such as sodium phosphate ($Na_3PO_4$) and potassium phosphate ($K_3PO_4$); and organic salts such as ammonium salts such as triethylamines, pyridine, morpholine, quinoline, piperidine, DBU (diazabicycloundecene), anilines and tetra-n-butylammonium acetate. These bases can be used alone or in combination.

Also, in this reaction, examples of the reaction solvent containing an alkoxy alcohol include alkoxy alcohol, or a mixed solvent of an alkoxy alcohol and other solvents.

Examples of the alkoxy alcohol include 2-methoxy-1-propanol, 2-ethoxy-1-propanol, ethylene glycol monomethyl ether, ethylene glycol monoethyl ether and ethylene glycol isopropyl ether. These alkoxy alcohols may be used alone or in combination. Examples of the other solvents include aqueous solvents, for example, water and alcohols such as methanol, ethanol and isopropanol (IPA). These other solvents may be used alone or in combination.

Also, in this reaction, a mixing ratio of the compound represented by the above general formula (1) to the compound represented by the above general formula (2) or (3) is not specifically limited. But, for example, the compound represented by the general formula (2) or (3) is mixed in an amount of 0.1 to 10 equivalents, and preferably 0.5 to 2 equivalents, based on the compound represented by the general formula (1).

Further, in this reaction, the palladium-containing perovskite-type composite oxide is not specifically limited, but is added in an amount of 0.001 to 10 mol %, and preferably 0.001 to 5 mol %, in terms of the palladium content.

In this reaction, the base is not specifically limited, but is added in an amount of 1 to 30 equivalents, and preferably 1 to 10 equivalents.

Also, in this reaction, the reaction solvent containing an alkoxy alcohol is not specifically limited, but is added in an amount of 100 to 300 parts by weight, and preferably 500 to 1,000 parts by weight, based on 100 parts by weight of the mixing amount of the compound represented by the general formula (1) and the compound represented by the general formula (2) or the compound represented by the general formula (3).

In case of using a mixed solvent of an alkoxy alcohol and other solvents as the reaction solvent containing an alkoxy alcohol, a volume ratio of the alkoxy alcohol to the other solvent, alkoxy alcohol/the other solvent, is from 1/5 to 5/1, and preferably 1/1.

This reaction is carried out, for example, under a reaction pressure of 0 to 5,000 KPa, and preferably from 0 to 3,000 KPa, at a reaction temperature of 0 to 250° C., and preferably from 0 to 150° C., for a reaction time of 0.1 to 72 hours, and preferably from 0.5 to 24 hours.

Further, in this reaction, an additive can be used in order to accelerate the reaction. Examples of the additive include organic ammonium halides such as tetra-n-butylammonium bromide (TBAB). Incidentally, the additive is added in an amount of 1 to 200 mol %.

More specifically, in this reaction, a compound represented by the above general formula (1) and a compound represented by the above general formula (2) or (3) are, together with the palladium-containing perovskite-type composite oxide and a base, added to a reaction solvent containing an alkoxy alcohol in the above ratio, and reacted under the above reaction conditions, thereby to obtain a compound represented by the above general formula (14) or (17).

In the method of synthesizing a compound of the present invention, a compound represented by the above general formula (14) or (17) can be synthesized in a high yield through Suzuki Cross-Couplings, Stille Cross-Couplings or Heck Cross-Couplings in the presence of the palladium-containing perovskite-type composite oxide using the reaction solvent containing an alkoxy alcohol as described above.

Also, according to the method of synthesizing a compound of the present invention, in such a reaction, the palladium-containing perovskite-type composite oxide is in the form of a solid after the completion of the reaction and can be easily recovered from the reaction mixed solution by filtration or decantation. Moreover, the recovered palladium-containing perovskite-type composite oxide can be repeatedly used in this reaction without drastically deteriorating activity of the catalyst. Therefore, cost required for disposal of the catalyst can be reduced. As a result, production cost can be reduced. After using repeatedly, activity of the catalyst can be maintained and thus the reaction in a high yield can be achieved.

Therefore, the method of synthesizing a compound of the present invention can be effectively used in applications using Suzuki Cross-Couplings on the industrial basis, for example, synthesis of drugs having the following biphenyl skeletons.

[Chemical Formula 7]

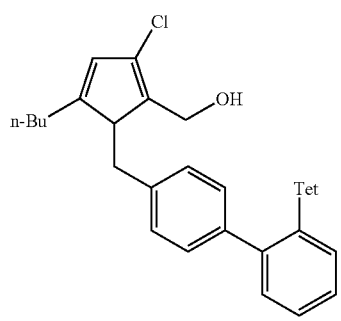

[Chemical Formula 8]

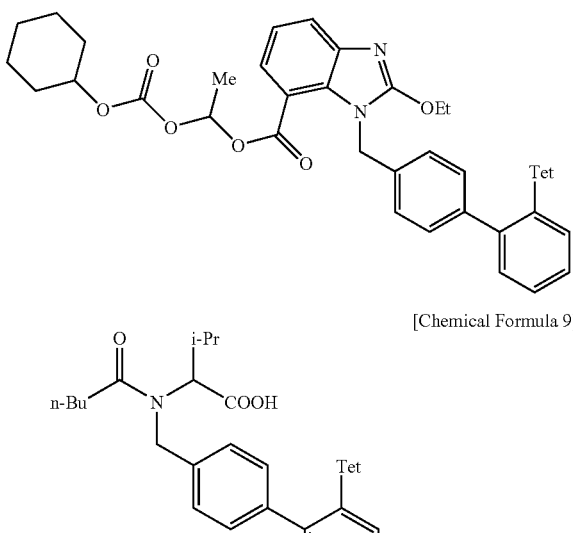

[Chemical Formula 9]

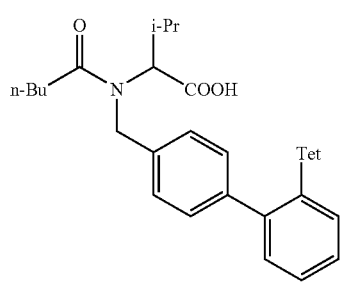

[Chemical Formula 10]

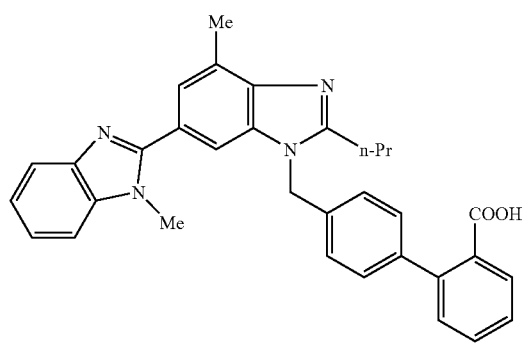

[Chemical Formula 11]

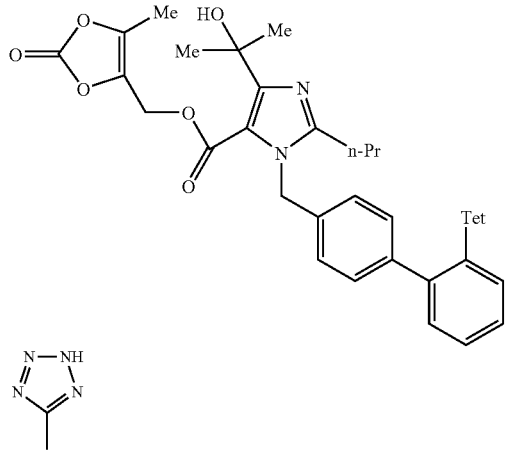

EXAMPLES

The present invention will now be described in more detail by way of Production Examples and Synthesis Examples, but are not limited thereto.

1) Production Examples of Synthesis Reaction Catalyst (Perovskite-Type Composite Oxide)

Production Example 1 (Production of $La_{1.00}Fe_{0.57}Co_{0.38}Pd_{0.05}O_3$)

| | |
|---|---|
| Lanthanum methoxypropylate | 40.6 g (0.100 mol) |
| Iron methoxypropylate | 18.4 g (0.057 mol) |
| Cobalt ethoxyethylate | 9.0 g (0.038 mol) |

A mixed alkoxide solution was prepared by charging the above components in a 500 mL round-bottomed flask, and dissolving them in 200 mL of toluene with stirring. Separately, 1.52 g (0.005 mol) of palladium acetylacetonate was dissolved in 100 mL of toluene, and the solution was added to the mixed alkoxide solution in the round-bottomed flask to prepare a homogeneous mixed solution containing LaFe-CoPd.

Next, 200 mL of deionized water was added dropwise into the round-bottomed flask over about 15 minutes. A viscous brown precipitate was formed on hydrolysis.

After stirring at room temperature for 2 hours, toluene and water were distilled off under reduced pressure to obtain a precursor of the LaFeCoPd composite oxide. Then, the precursor was transferred into a petri dish, and subjected to forced-air drying at 60° C. for 24 hours, followed by a primary heat treatment at 600° C. in the atmosphere for 2 hours and a secondary heat treatment at 1,000° C. for one hour using an electric furnace to obtain a blackish brown powder.

The X-ray powder diffraction of the powder was determined. The powder was identified as a single crystal phase comprising a composite oxide having a perovskite-type structure of $La_{1.00}Fe_{0.57}Co_{0.38}Pd_{0.05}O_3$. The specific surface area thereof was 2.2 m²/g.

Production Example 2 (Production of $La_{1.00}Fe_{0.95}Pd_{0.05}O_3$)

| Lanthanum methoxypropylate | 40.6 g (0.100 mol) |
|---|---|
| Iron methoxypropylate | 30.7 g (0.095 mol) |

A mixed alkoxide solution was prepared by charging the above components in a 500 mL round-bottomed flask, and dissolving them in 200 mL of toluene with stirring. Separately, 1.52 g (0.005 mol) of palladium acetylacetonate was dissolved in 100 mL of toluene, and the solution was added to the mixed alkoxide solution in the round-bottomed flask to prepare a homogeneous mixed solution containing LaFePd.

Hereinafter, in the same manner as in Production Example 1, a blackish brown powder was obtained.

The X-ray powder diffraction of the powder was determined. The powder was identified as a single crystal phase comprising a composite oxide having a perovskite-type structure of $La_{1.00}Fe_{0.95}Pd_{0.05}O_3$. The specific surface area thereof was 5.0 m$^2$/g.

Production Example 3 (Production of $La_{1.05}Fe_{0.57}Co_{0.38}Pd_{0.05}O_{3+\alpha}$)

| Lanthanum methoxypropylate | 42.6 g (0.105 mol) |
|---|---|
| Iron methoxypropylate | 18.4 g (0.057 mol) |
| Cobalt ethoxyethylate | 9.0 g (0.038 mol) |

A mixed alkoxide solution was prepared by charging the above components in a 500 mL round-bottomed flask, and dissolving them in 200 mL of toluene with stirring. Separately, 1.52 g (0.005 mol) of palladium acetylacetonate was dissolved in 100 mL of toluene, and the solution was added to the mixed alkoxide solution in the round-bottomed flask to prepare a homogeneous mixed solution containing LaFeCoPd.

Hereinafter, in the same manner as in Production Example 1, a blackish brown powder was obtained.

The X-ray powder diffraction of the powder was determined. The powder was identified as a single crystal phase comprising a composite oxide having a perovskite-type structure of $La_{1.05}Fe_{0.57}Co_{0.38}Pd_{0.05}O_{3+\alpha}$. The specific surface area thereof was 2.1 m$^2$/g.

Production Example 4 (Production of $La_{1.02}Fe_{0.95}Pd_{0.05}O_{3+\alpha}$)

| Lanthanum methoxypropylate | 41.4 g (0.102 mol) |
|---|---|
| Iron methoxypropylate | 30.7 g (0.095 mol) |

A mixed alkoxide solution was prepared by charging the above components in a 500 mL round-bottomed flask, and dissolving them in 200 mL of toluene with stirring. Separately, 1.52 g (0.005 mol) of palladium acetylacetonate was dissolved in 100 mL of toluene, and the solution was added to the mixed alkoxide solution in the round-bottomed flask to prepare a homogeneous mixed solution containing LaFePd.

Hereinafter, in the same manner as in Production Example 1, a blackish brown powder was obtained.

The X-ray powder diffraction of the powder was determined. The powder was identified as a single crystal phase comprising a composite oxide having a perovskite-type structure of $La_{1.02}Fe_{0.95}Pd_{0.05}O_{3+\alpha}$. The specific surface area thereof was 4.9 m$^2$/g.

2) Synthesis Example of 4-Methoxybiphenyl by Suzuki Cross-Couplings

In the presence of each of the Pd-containing perovskite-type composite oxides which were prepared in Production Examples 1 to 4, 4-bromoanisole and phenylboronic acid were reacted as shown in the following general formula (19).

[Chemical Formula 12]

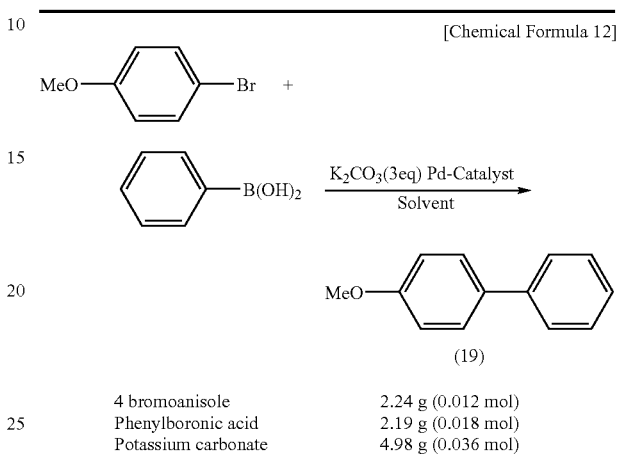

| 4 bromoanisole | 2.24 g (0.012 mol) |
|---|---|
| Phenylboronic acid | 2.19 g (0.018 mol) |
| Potassium carbonate | 4.98 g (0.036 mol) |

The above components were charged in a 100 mL round-bottomed flask and, as shown in Table 4, 18 mL of a mixed solvent of an alkoxy alcohol and deionized water (alkoxy alcohol/deionized water=1/1, vol/vol) as a reaction solvent in Examples and 18 mL of a mixed solvent of isopropyl alcohol and deionized water (isopropyl alcohol/deionized water=1/1, vol/vol) as a reaction solvent in Comparative Examples (36 mL in total) were added and dissolved with stirring. The palladium-containing perovskite-type composite oxide prepared in each of Production Examples 1 to 4 was added to the solution in an amount shown in Table 4. The resulting solution was heated in a mantle heater, and then heated to reflux at a reflux temperature shown in Table 4 for 10 hours.

After the completion of the reaction, the flask was cooled, and 20 mL of toluene was added therein to dissolve the reaction product. Insoluble matters were removed by suction filtration, and the toluene and the reaction solvent were distilled off under reduced pressure to precipitate a white solid product. Then, 20 mL of toluene and 20 mL of deionized water were added to the white solid product to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-methoxybiphenyl as a white crystal. The weight of the obtained white crystal was measured to calculate the crude yield. It was 102 to 112% (2.25 to 2.48 g). A portion of this crude crystal was dissolved in methanol and recrystallized, and then the resulting white crystal was analyzed. As a result, GC purity was 99.5%, a melting point was 88.0 to 89.5° C., and an elemental analysis value (C13, H12) was as follows: C=85.30%; H=6.01%. Then, 20 mL of toluene was added to the white crystal to dissolve it with stirring, and, using gas chromatography, the conversion rate was calculated according to the following equation.

Conversion rate (%)=4-methoxybiphenyl/(4-bromoanisole+4-methoxybiphenyl)×100

(each toluene solution of 4-methoxybiphenyl and 4-bromoanisole was measured to determine the relative sensitivity and a calibration correction was performed in advance.)

The results are shown in Table 4.

3) Measurement of Turnover Number

Aryl bromide (4-bromoanisole) represented by the above general formula (19) and boronicacid (phenylboronicacid) were reacted under the same reaction conditions as in Synthesis Examples. Using gas chromatography as mentioned above, the turnover number (TON) was calculated by the following equation in terms of mole number of the obtained 4-methoxybiphenyl per mol palladium.

Turnover number=4-methoxybiphenyl (mol)/palladium (mol)×conversion rate

The results are shown in Table 4.

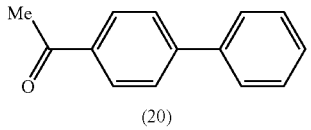

(20)

| 4-bromoacetophenone | 2.38 g (0.012 mol) |
| Phenylboronic acid | 2.19 g (0.018 mol) |
| Potassium carbonate | 4.98 g (0.036 mol) |

The above components were charged in a 100 mL round-bottomed flask and, as shown in Table 5, 18 mL of a mixed solvent of 2-methoxy-1-propanol and deionized water (2-methoxy-1-propanol/deionized water=1/1, vol/vol) as a reaction solvent in each of Examples and 18 mL of a mixed solvent of isopropyl alcohol and deionized water (isopropyl alcohol/deionized water=1/1, vol/vol) as a reaction solvent in each of Comparative Examples (36 mL in total) were added and dissolved with stirring. Each of the palladium-containing

TABLE 4

| | Pd-containing perovskite-type composite oxide | | | Reaction conditions | | |
| --- | --- | --- | --- | --- | --- | --- |
| | Composition | Specific surface area (m²/g) | Addition amount (Pd mol %) | Reaction solvent* | Reflux temperature (° C.) | Conversion rate (%) | TON (Pd$^{-1}$) |
| Example 1 | $La_{1.00}Fe_{0.57}Co_{0.38}Pd_{0.05}O_3$ | 2.2 | 0.025 | MP/H$_2$O | 100 | 97.6 | 3,904 |
| Example 2 | $La_{1.00}Fe_{0.95}Pd_{0.05}O_3$ | 5.0 | 0.003 | MP/H$_2$O | 100 | 92.8 | 30,933 |
| Example 3 | $La_{1.05}Fe_{0.57}Co_{0.38}Pd_{0.05}O_{3+\sigma}$ | 2.1 | 0.025 | MP/H$_2$O | 100 | 97.5 | 3,900 |
| Example 4 | $La_{1.02}Fe_{0.95}Pd_{0.05}O_{3+\sigma}$ | 4.9 | 0.003 | MP/H$_2$O | 100 | 93.0 | 31,000 |
| Example 5 | $La_{1.00}Fe_{0.57}Co_{0.38}Pd_{0.05}O_3$ | 2.2 | 0.025 | EGEE/H$_2$O | 104 | 96.0 | 3,840 |
| Example 6 | $La_{1.00}Fe_{0.95}Pd_{0.05}O_3$ | 5.0 | 0.003 | EGEE/H$_2$O | 104 | 92.2 | 30,733 |
| Example 7 | $La_{1.05}Fe_{0.57}Co_{0.38}Pd_{0.05}O_{3+\sigma}$ | 2.1 | 0.025 | EGEE/H$_2$O | 104 | 97.5 | 3,900 |
| Example 8 | $La_{1.02}Fe_{0.95}Pd_{0.05}O_{3+\sigma}$ | 4.9 | 0.003 | EGEE/H$_2$O | 104 | 93.0 | 31,000 |
| Example 9 | $La_{1.0}Fe_{0.57}Co_{0.38}Pd_{0.05}O_3$ | 4.3 | 0.001 | EGME/H$_2$O | 104 | 92.8 | 92,800 |
| Example 10 | $La_{1.0}Fe_{0.95}Pd_{0.05}O_3$ | 5.0 | 0.001 | EGME/H$_2$O | 104 | 96.7 | 96,700 |
| Com. Example 1 | $La_{1.00}Fe_{0.57}Co_{0.38}Pd_{0.05}O_3$ | 2.2 | 0.025 | IPA/H$_2$O | 80 | 85.6 | 3,424 |
| Com. Example 2 | $La_{1.00}Fe_{0.95}Pd_{0.05}O_3$ | 5.0 | 0.003 | IPA/H$_2$O | 80 | 84.0 | 28,000 |
| Com. Example 3 | $La_{1.05}Fe_{0.57}Co_{0.38}Pd_{0.05}O_{3+\sigma}$ | 2.1 | 0.025 | IPA/H$_2$O | 80 | 86.7 | 3,468 |
| Com. Example 4 | $La_{1.02}Fe_{0.95}Pd_{0.05}O_{3+\sigma}$ | 4.9 | 0.003 | IPA/H$_2$O | 80 | 85.1 | 28,367 |
| Com. Example 5 | $La_{1.0}Fe_{0.57}Co_{0.38}Pd_{0.05}O_3$ | 4.3 | 0.001 | IPA/H$_2$O | 80 | 68.3 | 68,300 |
| Com. Example 6 | $La_{1.0}Fe_{0.95}Pd_{0.05}O_3$ | 5.0 | 0.001 | IPA/H$_2$O | 80 | 70.5 | 70,500 |

*MP: 2-methoxy-1-propanol
EGEE: Ethylene glycol monoethyl ether
IPA: Isopropyl alcohol
EGME: Ethylene glycol monomethyl ether (methyl cellosolve)

4) Synthesis Example of 4-Acetylbiphenyl by Suzuki Cross-Couplings

In the presence of each of the Pd-containing perovskite-type composite oxides which were prepared in Production Examples 1 and 2, 4-bromoacetophenone and phenylboronic acid were reacted as shown in the following formula (20).

[Chemical Formula 13]

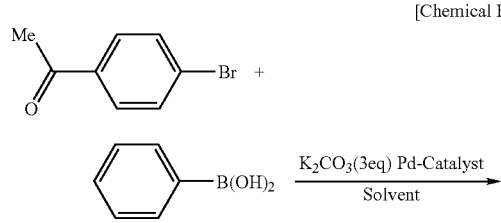

perovskite-type composite oxides prepared in Production Examples 1 and 2 was added to the solution in an amount shown in Table 5. The resulting solution was heated in a mantle heater, and then heated to reflux at a reflux temperature shown in Table 5 for 4 hours.

After the completion of the reaction, the flask was cooled, and 50 mL of toluene was added therein to dissolve the reaction product. Insoluble matters were removed by suction filtration, and the toluene and the reaction solvent were distilled off under reduced pressure to precipitate a white solid product. Then, 50 mL of toluene and 20 mL of deionized water were added to the white solid product to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-acetylbiphenyl as a white crystal. The weight of the obtained white crystal was measured to calculate the crude yield. It was 103 to 110%. Then, 20 mL of tetrahydrofuran was added to the white crystal to dissolve it with stirring, and, using gas chromatography, the conversion rate was calculated according to the following equation.

Conversion rate (%)=4-acetylbiphenyl/(4-bromoacetophenone+4-acetylbiphenyl)×100

(each toluene solution of 4-acetylbiphenyl and 4-bromoacetophenone was measured to determine the relative sensitivity and a calibration correction was performed in advance.)

The results are shown in Table 5.

The above components were charged in a 100 mL round-bottomed flask and, as shown in Table 6, 18 mL of a mixed solvent of ethylene glycol monomethyl ether (methyl cellosolve) and deionized water (ethylene glycol monomethyl ether/deionized water=1/1, vol/vol) as a reaction solvent in Examples and 18 mL of a mixed solvent of isopropyl alcohol and deionized water (isopropyl alcohol/deionized water=1/1, vol/vol) as a reaction solvent in Comparative Examples (36 mL in total) were added and dissolved with stirring. Each of the palladium-containing perovskite-type composite oxides prepared in Production Examples 1 and 2 was added to the solution in an amount shown in Table 6. The resulting solution was heated in a mantle heater, and then heated to reflux at a reflux temperature shown in Table 6 for 4 hours.

TABLE 5

| | Pd-containing perovskite-type composite oxide | | | Reaction conditions | | |
| --- | --- | --- | --- | --- | --- | --- |
| | Composition | Specific surface area (m$^2$/g) | Addition amount (Pd mol %) | Reaction solvent* | Reflux temperature (° C.) | Conversion rate (%) | TON (Pd$^{-1}$) |
| Example 11 | La$_{1.00}$Fe$_{0.57}$Co$_{0.38}$Pd$_{0.05}$O$_3$ | 4.3 | 0.001 | MP/H$_2$O | 100 | 97.2 | 97,200 |
| Example 12 | La$_{1.00}$Fe$_{0.95}$Pd$_{0.05}$O$_3$ | 5.0 | 0.001 | MP/H$_2$O | 100 | 100.0 | 100,000 |
| Com. Example 7 | La$_{1.00}$Fe$_{0.57}$Co$_{0.38}$Pd$_{0.05}$O$_3$ | 4.3 | 0.001 | IPA/H$_2$O | 80 | 42.6 | 42,600 |
| Com. Example 8 | La$_{1.00}$Fe$_{0.95}$Pd$_{0.05}$O$_3$ | 5.0 | 0.001 | IPA/H$_2$O | 80 | 54.2 | 54,200 |

*MP: 2-methoxy-1-propanol
IPA: Isopropyl alcohol

5) Synthesis Example of 4-Methylbiphenyl by Suzuki Cross-Couplings

In the presence of each of the Pd-containing perovskite-type composite oxides which were prepared in Production Examples 1 and 2, 4-bromotoluene and triphenylboroxine were reacted as shown in the following formula (21).

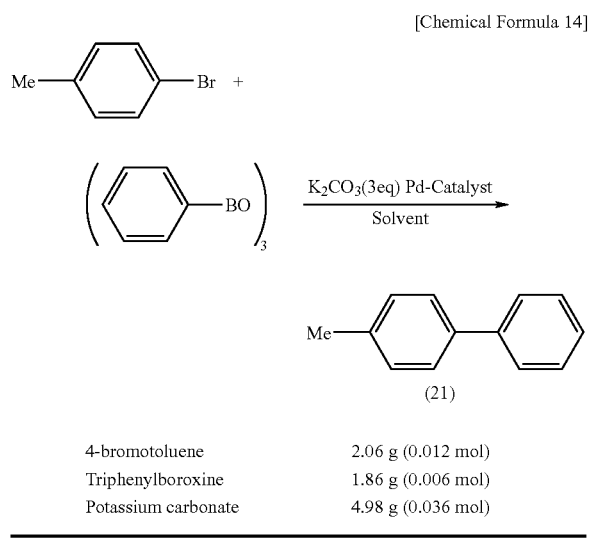

[Chemical Formula 14]

(21)

| 4-bromotoluene | 2.06 g (0.012 mol) |
| --- | --- |
| Triphenylboroxine | 1.86 g (0.006 mol) |
| Potassium carbonate | 4.98 g (0.036 mol) |

After the completion of the reaction, the flask was cooled, and 20 mL of toluene was added therein to dissolve the reaction product. Insoluble matters were removed by suction filtration, and the toluene and the reaction solvent were distilled off under reduced pressure to precipitate a white solid product. Then, 20 mL of toluene and 20 mL of deionized water were added to the white solid product to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-methylbiphenyl as a white crystal. The weight of the obtained white crystal was measured to calculate the crude yield. It was 104 to 115%. Then, 20 mL of toluene was added to the white crystal to dissolve it with stirring, and, using gas chromatography, the conversion rate was calculated according to the following equation.

Conversion rate (%)=4-methylbiphenyl/(4-bromotoluene+4-methylbiphenyl)×100

(each toluene solution of 4-methylbiphenyl and 4-bromotoluene was measured to determine the relative sensitivity and a calibration correction was performed in advance.)

The results are shown in Table 6.

TABLE 6

| | Pd-containing perovskite-type composite oxide | | | Reaction conditions | | | |
|---|---|---|---|---|---|---|---|
| | Composition | Specific surface area (m²/g) | Addition amount (Pd mol %) | Reaction solvent* | Reflux temperature (° C.) | Conversion rate (%) | TON (Pd⁻¹) |
| Example 13 | $La_{1.00}Fe_{0.57}Co_{0.38}Pd_{0.05}O_3$ | 4.3 | 0.001 | EGME/H$_2$O | 104 | 100.0 | 100,000 |
| Example 14 | $La_{1.00}Fe_{0.95}Pd_{0.05}O_3$ | 5.0 | 0.001 | EGME/H$_2$O | 104 | 100.0 | 100,000 |
| Com. Example 9 | $La_{1.00}Fe_{0.57}Co_{0.38}Pd_{0.05}O_3$ | 4.3 | 0.001 | IPA/H$_2$O | 80 | 67.5 | 67,500 |
| Com. Example 10 | $La_{1.00}Fe_{0.95}Pd_{0.05}O_3$ | 5.0 | 0.001 | IPA/H$_2$O | 80 | 70.8 | 70,800 |

*EGME: Ethylene glycol monomethyl ether (methyl cellosolve)
IPA: Isopropyl alcohol 6) Synthesis Example of 4-Methoxy-4'-Methylbiphenyl by Suzuki Cross-Couplings In the presence of each of the palladium-containing perovskite-type composite oxides which were prepared in Production Examples 1 and 2, 4-bromoanisole and 4-methylphenylboronic acid were reacted as shown in the following formula (22).

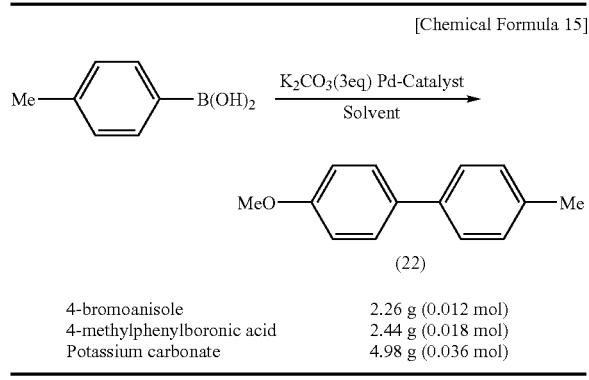

[Chemical Formula 15]

| 4-bromoanisole | 2.26 g (0.012 mol) |
| 4-methylphenylboronic acid | 2.44 g (0.018 mol) |
| Potassium carbonate | 4.98 g (0.036 mol) |

The above components were charged in a 100 mL round-bottomed flask and, as shown in Table 7, 18 mL of a mixed solvent of 2-methoxy-1-propanol and deionized water (2-methoxy-1-propanol/deionized water=1/1, vol/vol) as a reaction solvent in each of Examples and 18 mL of a mixed solvent of isopropyl alcohol and deionized water (isopropyl alcohol/deionized water=1/1, vol/vol) as a reaction solvent in each of Comparative Examples (36 mL in total) were added and dissolved with stirring. Each of the palladium-containing perovskite-type composite oxides prepared in Production Examples 1 and 2 was added to the solution in an amount shown in Table 7. The resulting solution was heated in a mantle heater, and then heated to reflux at a reflux temperature shown in Table 7 for 4 hours.

After the completion of the reaction, the flask was cooled, and 20 mL of toluene was added therein to dissolve the reaction product. Insoluble matters were removed by suction filtration, and the toluene and the reaction solvent were distilled off under reduced pressure to precipitate a white solid product. Then, 20 mL of toluene and 20 mL of deionized water were added to the white solid product to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-methoxy-4'-methylbiphenyl as a white crystal. The weight of the obtained white crystal was measured to calculate the crude yield. It was 106 to 115%. Then, 20 mL of toluene was added to the white crystal to dissolve it with stirring, and, using gas chromatography, the conversion rate was calculated according to the following equation.

Conversion rate (%)=4-methoxy-4'-methylbiphenyl/
(4-bromoanisole+4-methoxy-4'-methylbiphenyl)×100

(each toluene solution of 4-methoxy-4'-methylbiphenyl and 4-bromoanisole was measured to determine the relative sensitivity and a calibration correction was performed in advance.)

The results are shown in Table 7.

TABLE 7

| | Pd-containing perovskite-type composite oxide | | | Reaction conditions | | | |
|---|---|---|---|---|---|---|---|
| | Composition | Specific surface area (m²/g) | Addition amount (Pd mol %) | Reaction solvent* | Reflux temperature (° C.) | Conversion rate (%) | TON (Pd⁻¹) |
| Example 15 | $La_{1.00}Fe_{0.57}Co_{0.38}Pd_{0.05}O_3$ | 4.3 | 0.001 | MP/H$_2$O | 100 | 84.5 | 84,500 |
| Example 16 | $La_{1.00}Fe_{0.95}Pd_{0.05}O_3$ | 5.0 | 0.001 | MP/H$_2$O | 100 | 88.3 | 88,300 |
| Com. Example 11 | $La_{1.00}Fe_{0.57}Co_{0.38}Pd_{0.05}O_3$ | 4.3 | 0.001 | IPA/H$_2$O | 80 | 45.7 | 45,700 |
| Com. Example 12 | $La_{1.00}Fe_{0.95}Pd_{0.05}O_3$ | 5.0 | 0.001 | IPA/H$_2$O | 80 | 55.8 | 55,800 |

*MP: 2-methoxy-1-propanol
IPA: Isopropyl alcohol

7) Synthesis Example of 4-Nitrobiphenyl by Suzuki Cross-Couplings

In the presence of the palladium-containing perovskite-type composite oxide which was prepared in Production Example 2, 4-bromonitrobenzene and phenylboronic acid were reacted as shown in the following formula (23).

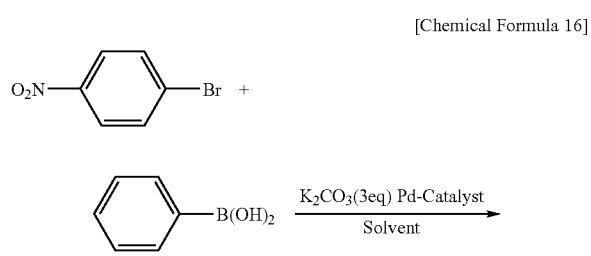

[Chemical Formula 16]

-continued

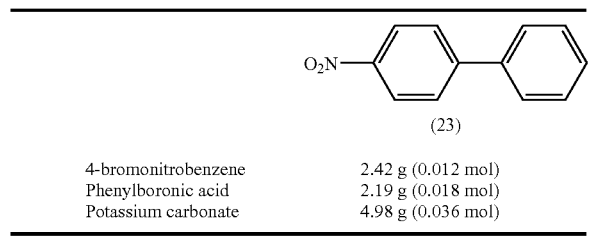

(23)

| 4-bromonitrobenzene | 2.42 g (0.012 mol) |
| Phenylboronic acid | 2.19 g (0.018 mol) |
| Potassium carbonate | 4.98 g (0.036 mol) |

The above components were charged in a 100 mL round-bottomed flask and, as shown in Table 8, 18 mL of a mixed solvent of ethylene glycol monomethyl ether (methyl cellosolve) and deionized water (ethylene glycol monomethyl ether/deionized water=1/1, vol/vol) as a reaction solvent in each of Examples and 18 mL of a mixed solvent of isopropyl alcohol and deionized water (isopropyl alcohol/deionized water=1/1, vol/vol) as a reaction solvent in each of Comparative Examples (36 mL in total) were added and dissolved with stirring. The palladium-containing perovskite-type composite oxide prepared in Production Example 2 was added to the solution in an amount shown in Table 8. The resulting solution was heated in a mantle heater, and then heated to reflux at a reflux temperature shown in Table 8 for 4 hours.

After the completion of the reaction, the flask was cooled, and 20 mL of toluene was added therein to dissolve the reaction product. Insoluble matters were removed by suction filtration, and the toluene and the reaction solvent were distilled off under reduced pressure to precipitate a white solid product. Then, 20 mL of toluene and 20 mL of deionized water were added to the white solid product to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-nitrobiphenyl as a yellow crystal. The weight of the obtained yellow crystal was measured to calculate the crude yield. It was 107 to 113%. Then, 20 mL of toluene was added to the yellow crystal to dissolve it with stirring, and, using gas chromatography, the conversion rate was calculated according to the following equation.

Conversion rate (%)=4-nitrobiphenyl/(4-bromonitrobenzene+4-nitrobiphenyl)×100

(each toluene solution of 4-nitrobiphenyl and 4-bromonitrobenzene was measured to determine the relative sensitivity and a calibration correction was performed in advance.)

The results are shown in Table 8.

TABLE 8

| | Pd-containing perovskite-type composite oxide | | | Reaction conditions | | |
| | Composition | Specific surface area (m$^2$/g) | Addition amount (Pd mol %) | Reaction solvent* | Reflux temperature (° C.) | Conversion rate (%) | TON (Pd$^{-1}$) |
| --- | --- | --- | --- | --- | --- | --- | --- |
| Example 17 | La$_{1.00}$Fe$_{0.95}$Pd$_{0.05}$O$_3$ | 5.0 | 0.001 | EGME/H$_2$O | 104 | 100.0 | 100,000 |
| Com. Example 13 | La$_{1.00}$Fe$_{0.95}$Pd$_{0.05}$O$_3$ | 5.0 | 0.001 | IPA/H$_2$O | 80 | 23.5 | 23,500 |

*EGME: Ethylene glycol monomethyl ether (methyl cellosolve)
IPA: Isopropyl alcohol 8) Synthesis Example of 4-Methoxybiphenyl by Stille Cross-Couplings In the presence of the palladium-containing perovskite-type composite oxide, which was prepared in Production Example 2, 4-bromoanisole and phenyltrimethyl tin were reacted as shown in the following formula (24).

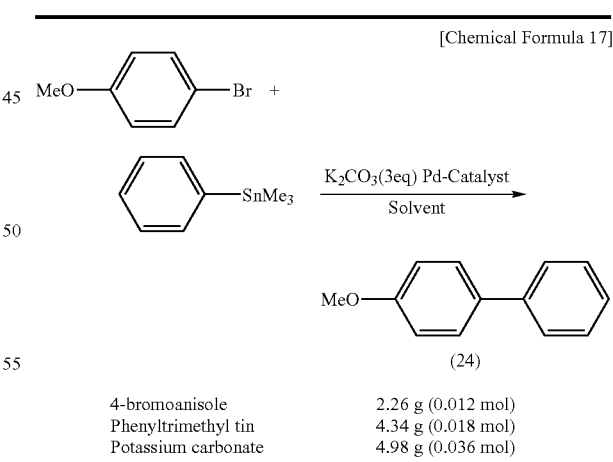

[Chemical Formula 17]

| 4-bromoanisole | 2.26 g (0.012 mol) |
| Phenyltrimethyl tin | 4.34 g (0.018 mol) |
| Potassium carbonate | 4.98 g (0.036 mol) |

The above components were charged in a 100 mL round-bottomed flask and, as shown in Table 9, 18 mL of a mixed solvent of ethylene glycol monomethyl ether (methyl cellosolve) and deionized water (ethylene glycol monomethyl ether/deionized water=1/1, vol/vol) as a reaction solvent in each of Examples and 18 mL of a mixed solvent of isopropyl alcohol and deionized water (isopropyl alcohol/deionized water=1/1, vol/vol) as a reaction solvent in each of Comparative Examples (36 mL in total) were added and dissolved with stirring. The palladium-containing perovskite-type composite oxide prepared in Production Example 2 was added to the solution in an amount shown in Table 9. The resulting solution was heated in a mantle heater, and then heated to reflux at a reflux temperature shown in Table 9 for 8 hours.

After the completion of the reaction, the flask was cooled, and 20 mL of toluene was added therein to dissolve the reaction product. Insoluble matters were removed by suction filtration, and the toluene and the reaction solvent were distilled off under reduced pressure to precipitate a white solid product. Then, 20 mL of toluene and 20 mL of deionized water were added to the white solid product to dissolve it, and the resulting solution was transferred into a separatory funnel. The lower aqueous layer was separated, and furthermore, 20 mL of deionized water was added to the remaining layer to wash it, and separated. Then, 5 g of sodium sulfate was added to the remaining layer, and then it was shaken well. After dehydration and drying, insoluble matters were removed by filtration, and the solvent was distilled off from the filtrate to obtain the objective 4-methoxybiphenyl as a white crystal. The weight of the obtained white crystal was measured to calculate the crude yield. It was 102 to 111%. Then, 20 mL of toluene was added to the white crystal to dissolve it with stirring, and, using gas chromatography, the conversion rate was calculated according to the following equation.

Conversion rate (%)=4-methoxybiphenyl/(4-bromoanisole+4-methoxybiphenyl)×100

(each toluene solution of 4-methoxybiphenyl and 4-bromoanisole was measured to determine the relative sensitivity, and a calibration correction was performed in advance.)

The results are shown in Table 9.

-continued

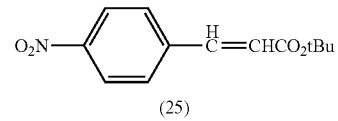

(25)

| | |
|---|---|
| 4-bromonitrobenzene | 2.42 g (0.012 mol) |
| Tert-butyl acrylate | 2.30 g (0.018 mol) |
| Sodium acetate | 2.88 g (0.036 mol) |

The above components were charged in a 100 mL round-bottomed flask, as shown in Table 10, 60 mL of 2-methoxy-1-propanol alone as a reaction solvent in each of Examples and 60 mL of isopropyl alcohol alone as a reaction solvent in each of Comparative Examples were added and dissolved with stirring. The palladium-containing perovskite-type composite oxide prepared in Production Example 2 was added to the solution in an amount shown in Table 10. The resulting solution was heated in a mantle heater, and then heated to reflux at a reflux temperature shown in Table 10 for 6 hours.

After the completion of the reaction, the flask was cooled, and 20 mL of toluene was added therein to dissolve the reaction product. Insoluble matters were removed by suction filtration, and the toluene and the reaction solvent were distilled off under reduced pressure to precipitate a yellow solid product. Then, 40 mL of toluene and 20 mL of deionized water were added to the yellow solid product to dissolve it, and the resulting solution was transferred into a separatory funnel. The lower aqueous layer was separated, and furthermore, 20 mL of deionized water was added to the remaining layer to wash it, and separated. Then, 5 g of sodium sulfate

TABLE 9

| | Pd-containing perovskite-type composite oxide | | | Reaction conditions | | | |
|---|---|---|---|---|---|---|---|
| | Composition | Specific surface area (m²/g) | Addition amount (Pd mol %) | Reaction solvent* | Reflux temperature (° C.) | Conversion rate (%) | TON (Pd⁻¹) |
| Example 18 | La$_{1.00}$Fe$_{0.95}$Pd$_{0.05}$O$_3$ | 5.0 | 0.05 | EGME/H$_2$O | 104 | 88.3 | 1,766 |
| Com. Example 14 | La$_{1.00}$Fe$_{0.95}$Pd$_{0.05}$O$_3$ | 5.0 | 0.05 | IPA/H$_2$O | 80 | 12.6 | 252 |

*EGME: Ethylene glycol monomethyl ether (methyl cellosolve)
IPA: Isopropyl alcohol 9) Synthesis Example of Tert-Butyl 4-Nitrophenyl Acrylate by Heck Cross-Couplings In the presence of the Pd-containing perovskite-type composite oxide, which was prepared in Production Example 2, 4-bromonitrobenzene and tert-butyl acrylate were reacted as shown in the following formula (24).

[Chemical Formula 18]

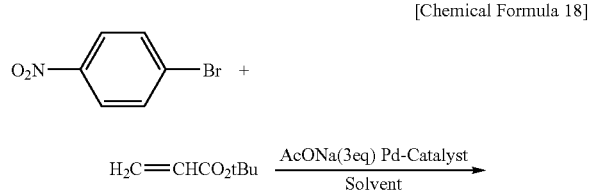

was added to the remaining layer, and then it was shaken well. After dehydration and drying, insoluble matters were removed by filtration, and the solvent was distilled off from the filtrate to obtain the objective tert-butyl 4-nitrophenyl acrylate as a yellow crystal. The structure of the product was confirmed by GC-MS. The weight of the obtained yellow crystal was measured to calculate the crude yield. It was 104 to 115%. Then, 20 mL of tetrahydrofuran (THF) was added to the yellow crystal to dissolve it with stirring, and, using gas chromatography, the conversion rate was calculated according to the following equation.

Conversion rate (%)=tert-butyl 4-nitrophenyl acrylate/(4-bromonitrobenzene+tert-butyl 4-nitrophenyl acrylate)×100

(each toluene solution of tert-butyl 4-nitrophenyl acrylate and 4-bromonitrobenzene was measured to determine the relative sensitivity and a calibration correction was performed in advance.)

The results are shown in Table 10.

TABLE 10

| | Pd-containing perovskite-type composite oxide | | | Reaction conditions | | |
|---|---|---|---|---|---|---|
| | Composition | Specific surface area (m²/g) | Addition amount (Pd mol %) | Reaction solvent* | Reflux temperature (° C.) | Conversion rate (%) | TON (Pd⁻¹) |
| Example 19 | La$_{1.00}$Fe$_{0.95}$Pd$_{0.05}$O$_3$ | 5.0 | 0.10 | MP | 122 | 97.4 | 974 |
| Com. Example 15 | La$_{1.00}$Fe$_{0.95}$Pd$_{0.05}$O$_3$ | 5.0 | 0.10 | IPA | 80 | 14.6 | 146 |

*MP: 2-methoxy-1-propanol
IPA: Isopropyl alcohol

While the illustrative embodiments and examples of the present invention are provided in the above description, such is for illustrative purpose only and it is not to be construed limitative. Modification and variation of the present invention which will be obvious to those skilled in the art is to be covered in the following claims.

INDUSTRIAL APPLICABILITY

As described above, the method of synthesizing a compound of the present invention is effectively applied when a palladium-containing perovskite-type composite oxide is used as a catalyst in a coupling reaction such as Suzuki Cross-Couplings, Stille Cross-Couplings or Heck Cross-Couplings.

The invention claimed is:

1. A method of synthesizing a compound, which comprises reacting a compound represented by the following general formula (1) with a compound represented by the following general formula (2), to produce a compound of formula $R_1$-$R_2$, or with a compound represented by the following general formula (3), to produce a compound of formula $R_1R_3C\!\!=\!\!CR_4R_5$, in the presence of a palladium-containing perovskite-type composite oxide using a reaction solvent comprising an alkoxy alcohol:

$$R_1\text{---}X \quad (1)$$

wherein $R_1$ represents an aryl group which may have a substituent, a heterocyclic group which may have a substituent, or an alkenyl group which may have a substituent; and X represents a halogen atom, a trifluoromethanesulfonyloxy group, a p-toluenesulfonyloxy group or a methanesulfonyloxy group, $$R_2\text{---}M \quad (2)$$

wherein $R_2$ represents an aryl group which may have a substituent, a heterocyclic group which may have a substituent, or an alkenyl group which may have a substituent; M represents a —B(ORa)$_2$— group or a —Sn(Rb)$_3$ group; Ra represents a hydrogen atom or an alkyl group which may have a substituent; and Rb represents an alkyl group, and instead of Ra, a ring including —OBO— may be formed through an arylene group which may have a substituent or an alkylene group which may have a substituent, both of which serve as a bond of —OBO—, and $$R_3HC\!\!=\!\!CR_4R_5 \quad (3)$$

wherein $R_3$, $R_4$ and $R_5$ each independently represents a hydrogen atom, an alkyl group which may have a substituent, an aryl group which may have a substituent, a carboxylic acid derivative, an acid amide derivative or a cyano group.

2. The method of synthesizing a compound according to claim 1, wherein a compound represented by the above general formula (1) is reacted with a compound represented by the above general formula (2) in the presence of a palladium-containing perovskite-type composite oxide, and wherein $R_1$ is an aryl group which may have a substituent and X is a halogen atom in the general formula (1), and $R_2$ is an aryl group which may have a substituent and M is a —B(ORa)$_2$ group in the general formula (2).

3. The method of synthesizing a compound according to claim 1, wherein the alkoxy alcohol is at least one selected from the group consisting of 2-methoxy-1-propanol, 2-ethoxy-1-propanol, ethylene glycol monomethyl ether, ethylene glycol monoethyl ether and ethylene glycol isopropyl ether.

4. The method of synthesizing a compound according to claim 1, wherein the palladium-containing perovskite-type composite oxide is represented by the following general formula (4):

$$A_xB_{(1-y)}Pd_yO_{3+\sigma} \quad (4)$$

wherein A represents at least one element selected from rare earth elements and alkaline earth metals, B represents at least one element selected from transition elements (excluding rare earth elements and Pd) and Al; x represents an atomic ratio satisfying the following relation: $1.0 \leq x \leq 1.3$; y represents an atomic ratio satisfying the following relation: $0 < y \leq 0.5$; and σ represents an oxygen excess amount.

* * * * *